(12) United States Patent
Bigorra Llosas et al.

(10) Patent No.: US 7,786,319 B2
(45) Date of Patent: Aug. 31, 2010

(54) ASYMMETRIC CATIONIC SURFACTANTS

(75) Inventors: Joaquin Bigorra Llosas, Sabadell (ES); Ansgar Behler, Bottrop (DE); Cristina Amela Conesa, Cerdanyola del Vallés (ES)

(73) Assignee: Cognis IP Management GmbH, Duesseldorf (DE)

( * ) Notice: Subject to any disclaimer, the term of this patent is extended or adjusted under 35 U.S.C. 154(b) by 161 days.

(21) Appl. No.: 12/039,932

(22) Filed: Feb. 29, 2008

(65) Prior Publication Data

US 2008/0214850 A1 Sep. 4, 2008

(30) Foreign Application Priority Data

Mar. 2, 2007 (EP) .................... 07004302

(51) Int. Cl.
*C07C 229/00* (2006.01)
(52) U.S. Cl. .................... 554/110; 554/114; 424/401
(58) Field of Classification Search ........... 554/110, 554/114

See application file for complete search history.

(56) References Cited

U.S. PATENT DOCUMENTS

| | | | |
|---|---|---|---|
| 4,456,554 A | 6/1984 | Walz et al. | |
| 5,349,106 A | 9/1994 | Behler et al. | |
| 5,609,167 A | 3/1997 | Hensen et al. | |
| 5,670,677 A | 9/1997 | Obiols et al. | |
| 5,869,716 A | 2/1999 | Pi Subirana et al. | |
| 5,886,201 A * | 3/1999 | Bonastre et al. | 554/110 |
| 2003/1161808 | 8/2003 | Bigorra Llosas et al. | |

FOREIGN PATENT DOCUMENTS

| | | |
|---|---|---|
| DE | 4026184 | 2/1992 |
| DE | 4 308 792 | 4/1994 |
| DE | 4409322 | 4/1995 |
| DE | 199 02 528 | 8/2000 |
| EP | 0 644 179 | 3/1995 |
| EP | 0614349 | 2/1996 |
| JP | 09 278728 | 10/1997 |
| JP | 2002 327195 | 11/2002 |
| WO | WO 91/01295 | 2/1991 |
| WO | WO 93/10748 | 6/1993 |

OTHER PUBLICATIONS

Ponsati, "Comunicaciones", C. R. CED-Congress, Barcelona, 1992, pp. 167-179.
Puchta et al., "A New Generation of Softeners," Tens. Surf. Det. 30, 1993, pp. 186-191.
Brock et al., "Neue Entwicklungen auf dem Gebiet der Wäscheweichspüler," Tens. Surf. Det. 30, 1993, pp. 394, 396, 398.
Lagerman et al., "Synthesis and Performance of Ester Quaternary Biodegradable Softeners," J. Am. Oil. Chem. Soc., vol. 71, 1994, pp. 97-100.
Falbe (ed.), "Surfactants in Consumer Products", Springer Verlag, Berlin, 1987, pp. 54-124.
Falbe (ed.), "Katalysatoren, Tenside und Mineralöladditive", Thieme Verlag, Stuttgart, 1978, pp. 123-217.
Todd et al., "Volatile silicone fluids for cosmetic formulations," Cosm. Toil. vol. 91, 1976, pp. 29-32.
Kosmetikverordnung, Appendix 6, Parts A and B, 1991.
"Kosmetische Färbemittel" of the Farbstoffkommission der Deutschen Forschungsgemeinschaft, Verlag Chemie, Weinheim, 1984, pp. 81-106.
Newman et al., "A Quantitative Characterization of Combing Force," J. Soc. Cosm. Chem., vol. 24, 1973, pp. 773-778, 780-782.

* cited by examiner

*Primary Examiner*—Deborah D Carr

(57) ABSTRACT

A process for preparing esterquats with asymmetric side chains, including the steps of: (a) reacting one or more alkanolamines with a mixture, including: (i) 30:70% b.w. of one or more $C_6$-$C_{10}$ monocarboxylic acids, and (ii) 70:30% b.w. of one or more $C_{12}$-$C_{22}$ monocarboxylic acids, and (b) quaternizing the resulting esters with one or more alkylation agents is provided.

A process for preparing esterquats with asymmetric side chains, including the steps of: esterifying a mixture of carboxylic acids with one or more alkanolamines to form a mixture of mono-, di- and trialkanolamine esters, where the mixture of carboxylic acids comprises (i) 30:70% b.w. of one or more $C_6$-$C_{10}$ monocarboxylic acids, and (ii) 70:30% b.w. of one or more $C_{12}$-$C_{22}$ monocarboxylic acids; and quaternizing the esters with one or more alkylation agents is also provided.

17 Claims, No Drawings

ASYMMETRIC CATIONIC SURFACTANTS

CROSS-REFERENCE TO RELATED APPLICATIONS

This application claims priority under 35 U.S.C. §119 from European Patent Application No. 07004302.1, filed Mar. 2, 2007, the entire disclosure of which is hereby incorporated by reference herein.

BACKGROUND OF THE INVENTION

1. Field of the Invention

The present invention relates generally to cationic surfactants, and more particularly, relates to cationic surfactants with asymmetric side chains, especially useful for cosmetic compositions, particularly applications in hair and skin care.

2. Background Information

"Esterquats" are generally understood to be quaternized fatty acid triethanolamine ester salts which are broadly suitable both for softening fibers and for conditioning hair. In the last decade, these substances have significantly displaced conventional quaternary ammonium compounds from the market, for example, distearyl dimethyl ammonium chloride, by virtue of their better ecotoxicological compatibility. Reviews of this subject have been published since the early 1990s, for example, by O. Ponsati in C. R. CED-Congress, Barcelona, 1992, page 167, by R. Puchta et al. in Tens. Surf. Det. 30, 186 (1993), by M. Brock in Tens. Surf. Det. 30, 394 (1993) and by R. Lagerman et al. in J. Am. Oil. Chem. Soc., 71, 97 (1994). Since that time, various types of esterquats and also "amidequats" have been synthesized so that an extensive state of the art is now available for the one looking for an adequate esterquat to solve his specific problem. Nevertheless, one can still find gaps where the products known from the market or from the literature do not meet the requirements of the market, especially in cases where the customer expects that the products fit into a complex profile.

For example, EP 00614349 B1 (Henkel) discloses acidic hair care compositions comprising esterquats and fatty alcohol (polyglycol ethers). The esterquats may be obtained from fatty acids comprising 6 to 22 carbon atoms, however, the preferred acids include at least 12 carbon atoms. Also, the working examples are limited to those esterquats which were obtained from technical grade C16/18 fatty acids based on beef tallow or palm oil. The reference discloses only those species having long or medium, and therefore, symmetric, side chains. The disadvantage associated with the use of such esterquats comes from the fact that on one hand viscosity is too high and too unstable for the formulation of pump sprays, and the application properties, in particular, combability and softening performance, leave room for improvement.

There remains a need for esterquats which overcome the disadvantages mentioned above.

SUMMARY OF THE INVENTION

Briefly described, according to an aspect of the invention, a process for preparing esterquats with asymmetric side chains, includes the steps of: (a) reacting one or more alkanolamines with a mixture, including: (i) 30:70% b.w. of one or more $C_6$-$C_{10}$ monocarboxylic acids, and (ii) 70:30% b.w. of one or more $C_{12}$-$C_{22}$ monocarboxylic acids, and (b) quaternizing the resulting esters with one or more alkylation agents is provided.

According to another aspect of the invention, a process for preparing esterquats with asymmetric side chains, includes the steps of: esterifying a mixture of carboxylic acids with one or more alkanolamines to form a mixture of mono-, di- and trialkanolamine esters, where the mixture of carboxylic acids comprises (i) 30:70% b.w. of one or more $C_6$-$C_{10}$ monocarboxylic acids, and (ii) 70:30% b.w. of one or more $C_{12}$-$C_{22}$ monocarboxylic acids; and quaternizing the esters with one or more alkylation agents is also provided.

DETAILED DESCRIPTION OF THE INVENTION

The present invention relates to esterquats with asymmetric side chains, obtainable by reacting alkanolamines with a mixture of (i) 30:70% b.w. of $C_6$-$C_{10}$ monocarboxylic acids, and (ii) 70:30% b.w. of $C_1$-$C_{22}$ monocarboxylic acids, and quaternizing the resulting esters with alkylation agents, optionally after alkoxylation.

Surprisingly, it has been observed that replacing the medium/long chain fatty acid moieties, as known from the state of the art, with a well-balanced mixture of short chain and medium/long chain fatty acids, which changes the structure of the molecule by the incorporation of asymmetric side chains, solves the problem which underlies the present invention.

Manufacturing Process

The esterquats with asymmetric side chains according to the present invention represent new cationic surfactants. More particularly, the esterquats are obtained by reacting alkanol amines with defined mixtures of short chain fatty acids and medium/long chain fatty acids and quaternizing the resulting esters with alkylation agents in known manner, optionally after alkoxylation.

According to the present invention, suitable esterquats are derived from alkanolamines following general formula (I):

(I)

wherein $R^1$ represents a hydroxyethyl radical, and $R^2$ and $R^3$ independently from each other represent a hydrogen, methyl or a hydroxyethyl radical. Typical examples are methyldiethanolamine (MDA), monoethanolamine (MES), diethanolamine (DEA) and triethanolamine (TEA). In a preferred embodiment of the present invention, triethanolamine is used as the starting material.

In a further preferred embodiment of the present invention, mixtures of (i) monocarboxylic acids selected from the group consisting of caproic acid, caprylic acid, 2-ethyl hexanoic acid, caprinic acid and mixtures thereof; and (ii) monocarboxylic acids selected from the group consisting of lauric acid, myristic acid, palmitic acid, stearic acid, oleic acid, behenic acid, erucic acid, and mixtures thereof, may be used.

It should be understood that the fatty acids representing group (i) and (ii) may also encompass technical grade fatty acids mixtures which can be derived from the splitting of fats and oils, optionally after additional separation and distillation, and therefore may include also other species.

It has been found rather advantageous with respect to the properties of the surfactants in the final hair or skin care products to use the monocarboxylic acids of groups (i) and (ii) in molar ratios of about 30:70 to about 70:30, and preferably in a ratio of about 50:50. The most preferred esterquats are obtained from mixtures consisting of caprylic acid and stearic acid, particularly when used in molar ratios of about 30:70 to 70:30.

The trialkanolamines and the fatty acid mixtures may be used in a molar ratio of 1:1 to 1:2.2. A molar ratio of trialkanolamine to acids of 1:1.5 to 1:2 has proven to be optimal. The esterification may be carried out in known manner, for example as described in International Patent application WO 91/01295 (Henkel). In one advantageous embodiment, it is carried out at temperatures between 120° C. and 220° C., and more particularly from 130° C. to 170° C., under pressures of 0.01 to 1 bar. Suitable catalysts are hypophosphorous acids and alkali metal salts thereof, preferably sodium hypophosphite, which may be used in quantities of 0.01 to 0.1% by weight, and preferably in quantities of about 0.05 to about 0.07% b.w., based on the starting materials. In the interests of particularly high color quality and stability, it has proven to be of advantage to use, as co-catalysts, alkali metal and/or alkaline earth metal borohydrides, for example potassium, magnesium and, in particular, sodium borohydride. The co-catalysts are normally used in quantities of about 50 to about 1000 ppm, and more particularly in quantities of about 100 to about 500 ppm, based on the starting materials. Corresponding processes are also the subject of DE 4308792 C1 and DE 4409322 C1 (Henkel) to which incorporation by reference is hereby specifically made. Alternatively, the esterification may be carried out with the two components in successive steps.

Asymmetric esterquats containing polyalkylene oxide may be produced by two methods. First, ethoxylated trialkanolamines may be used. This has the advantage that the distribution of alkylene oxide in the resulting esterquat is substantially the same in regard to the three OH groups of the amine. However, it also has the disadvantage that the esterification reaction is more difficult to carry out on steric grounds. Accordingly, the preferred method is to alkoxylate the ester before quaternization. This may be done in known manner, i.e., in the presence of basic catalysts and at elevated temperatures. Suitable catalysts are, for example, alkali metal and alkaline earth metal hydroxides and alcoholates, preferably sodium hydroxide, and more preferably, sodium methanolate. The catalysts are normally used in quantities of 0.5 to 5% by weight, and preferably in quantities of 1 to 3% by weight, based on the starting materials. Where these catalysts are used, free hydroxyl groups are primarily alkoxylated. However, if calcined hydrotalcites or hydrotalcites hydrophobicized with fatty acids are used as catalysts, the alkylene oxides are also inserted into the ester bonds. This method is preferred where the required alkylene oxide distribution approaches the one obtained in which alkoxylated trialkanolamines are used. Ethylene and propylene oxide and mixtures thereof (random or block distribution) may be used as alkylene oxides. The reaction is normally carried out at temperatures in the range from 100° C. to 180° C. The incorporation of, on average, 1 to 10 moles of alkylene oxide per mole of ester increases the hydrophilicity of the esterquat, improves solubility and reduces reactivity to anionic surfactants.

The quaternization of the fatty acid trialkanolamine esters may be carried out in a known manner. Although the reaction with the alkylation agents may also be carried out in the absence of solvents, it is advisable to use at least small quantities of water or lower alcohols, preferably isopropyl alcohol, for the production of concentrates which have a solids content of at least 80% by weight, and more particularly, at least 90% by weight. Suitable alkylation agents are alkyl or aryl halides such as, for example, methyl chloride, or benzyl chloride, dialkyl sulfates, such as, for example, dimethyl sulfate or diethyl sulphate, dialkyl carbonates, such as, for example, dimethyl carbonate or diethyl carbonate. The esters and the alkylating agents are normally used in amounts of 95 to 105 Mol-%, calculated on the molar amount of nitrogen within the ester mixture, i.e., in a substantially stoichiometric ratio. The reaction temperature is usually in the range from 40° C. to 80° C., and more particularly, in the range from 50° C. to 60° C. After the reaction, it is advisable to destroy unreacted alkylation agent by addition of, for example, ammonia, an (alkanol)amine, an amino acid or an oligopeptide, as described, for example, in DE 14026184 A1 (Henkel).

Industrial Application

The present invention also relates to the use of the esterquats with asymmetric side chains for making cosmetic compositions, such as, for example, a skin care or hair care composition, in particular, shampoos or conditioners, in which the esterquats may be present in amounts of 1 to 20, preferably 2 to 15, and more preferably 5 to 10% b.w., calculated on the final composition.

Cosmetic Compositions

The compositions comprising the new esterquats with asymmetric side chains may contain co-surfactants, oil bodies, emulsifiers, superfatting agents, pearlizing waxes, consistency factors, polymers, silicone compounds, waxes, stabilizers, primary and secondary sun protection agents, antidandruff agents, biogenic agents, film formers, swelling agents, hydrotropes, preservatives, solubilizers, complexing agents, reducing agents, alkalising agents, perfume oils, dyes, and the like, as additional auxiliaries and additives.

Co-Surfactants

Other preferred auxiliaries and additives are anionic and/or amphoteric or zwitteronic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)" Thieme Verlag, Stuttgart, 1978, pages 123-217. The percentage content of surfactants in the preparations may be from 0.1 to 10% by weight, and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18 carbon atoms, preferably 8 to 10 carbon atoms, esters of linear $C_6$-$C_{22}$-fatty acids with linear or branched $C_6$-$C_{22}$-fatty alcohols, or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$ fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (CETIOL® CC), Guerbet carbonates, based on fatty alcohols having 6 to 18, preferably 8 to 10, carbon atoms, esters of benzoic acid with linear and/or branched $C_6$-$C_{22}$-alcohols (e.g. FINSOLV® TN), linear or branched, symmetrical or asymmetrical dialkyl ethers having 6 to 22 carbon atoms per alkyl group, such as, for example, dicaprylyl ether (CETIOL® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including, for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono and diesters and sorbitan mono- and diesters of saturated and unsaturated fatty acids containing 6 to 22 carbon atoms and ethylene oxide addition products thereof, addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example, sorbitol), alkyl glucosides (for example, methyl glucoside, butyl glucoside, lauryl glucoside) and polyglucosides (for example, cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol;

polyalkylene glycols; and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantifies of triglyceride from the production process. Addition products of 1 to 30, and preferably 5 to 10, mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, and preferably 5 to 10, mol ethylene oxide onto the sorbitan esters mentioned are also suitable.

Polyglycerol Esters

Typical examples of suitable polyglycerol esters are Polyglyceryl-2 Dipolyhydroxystearate (DEYMULS® PGPH), Polyglycerin-3-Diisostearate (LAMEFORM® TGI), Polyglyceryl-4 Isostearate (ISOLAN® GI 34), Polyglyceryl-3 Oleate, Diisostearoyl Polyglyceryl-3 Diisostearate (ISOLAN® PDI), Polyglyceryl-3 Methylglucose Distearate (TEGO CARE® 450), Polyglyceryl-3 Beeswax (CERA BELLINA®), Polyglyceryl-4 Caprate (Polyglycerol Caprate T2010/90), Polyglyceryl-3 Cetyl Ether (CHIMEXANE® NL), Polyglyceryl-3 Distearate (CREMOPHOR® GS 32) and Polyglyceryl Polyricinoleate (ADMUL® WOL 1403), Polyglyceryl Dimerate Isostearate and mixtures thereof. Examples of other suitable polyolesters are the mono-, di- and tri-esters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, coooacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic adds containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents

Superfatting agents may be selected from such substances as, for example, lanolin and lecithin, and also polyethoxylated or acylated lanolin and lecithin derivatives, polyol fatty acid esters, monoglycerides and fatty acid alkanolamides, the fatty acid alkanolamides also serving as foam stabilizers.

Consistency Factors

The consistency factors mainly used are fatty alcohols or hydroxyfatty alcohols containing 12 to 22 carbon atoms, and preferably 16 to 18 carbon atoms, and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents

Suitable thickeners are polymeric thickeners, such as AEROSIL® types (hydrophilic silicas), polysaccharides, more especially xanthan gum, guar-guar, agar-agar, alginates and tyloses, carboxymethyl cellulose and hydroxyethyl cellulose, relatively high molecular weight polyethylene glycol monoesters and diesters of fatty acids, polyacrylates (for example CARBOPOLS® [Goodrich] or SYTHALENS® [Sigma]), polyacrylamides, polyvinyl alcohol and polyvinyl pyrrolidone, surfactants such as, for example, ethoxylated fatty acid glycerides, esters of fatty acids with polyols, for example, pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of POLYMER JR 400®, cationic starch, copolymers of diallyl ammonium salts and acrylamides, quaternized vinyl pyrrolidone/vinyl imidazole polymers such as, for example, LUVIQUAT® (BASF), condensation products of polyglycols and amines, quaternized collagen polypeptides such as, for example, Lauryldimonium Hydroxypropyl Hydrolyzed Collagen (LAMEQUAT® L, Grünau), quaternized wheat polypeptides, polyethyleneimine, cationic silicone polymers such as, for example, amodimethicone, copolymers of adipic acid and dimethylaminohydroxypropyl diethylenetriamine (CARTARETINE®, Sandoz), co-polymers of acrylic acid with dimethyl diallyl ammonium chloride (MERQUAT® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example, bis-dimethylamino-1,3-propane, cationic guar gum such as, for example, JAGUAR® CBS, JAGUAR® C-17, JAGUAR® C-16 of Celanese, quaternized ammonium salt polymers such as, for example, MIRAPOL® A-15, MIRAPOL® AD-1, MIRAPOL® AZ-1 of Miranol and the various polyquaternium types (for example 6, 7, 32 or 37) which can be found in the market under the tradenames RHEOCARE® CC or ULTRAGEL® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlizing waxes are, for example, alkylene glycol esters, especially ethylene glycol distearate; fatty acid alkanolamides, especially cocofatty acid diethanolamide;

partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amine, fatty acid-, alcohol, polyether-, epoxy-, fluorine, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes

In addition to natural oils, waxes may also be present in the preparations, more especially, natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Stabilizers

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example, heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;
  4-aminobenzoic acid derivatives, preferably 4-(dimethylamino)benzoic acid-2-ethylhexyl ester, 4-(dimethylamino)-benzoic acid-2-octyl ester and 4-(dimethylamino)benzoic acid amyl ester;
  esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocylene);
  esters of salicylic acid, preferably salicylic acid-2-ethylhexyl ester, salicylic acid-4-isopropylbenzyl ester, salicylic add homomethyl ester,
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzalmalonic acid, preferably 4-methoxybenzalmalonic acid di-2-ethylhexyl ester;
  triazine derivatives such as, for example, 2,4,6-trianilino-(p-carbo-2'-ethyl-1'-hexyloxy)-1,3,5-triazine and Octyl Triazone or Dioctyl Butamido Triazone (UVASORB® HEB);
  propane-1,3-diones such as, for example, 1-(4-tert.butylphenyl)-3-(4'-methoxyphenyl)-propane-1,3-dione; and
  ketotricyclo(5.2.1.0)decane derivatives.
  Suitable water-soluble substances are:
  2-phenylbenzimidazole-5-sulfonic acid and alkali metal, alkaline earth metal, ammonium, alkylammonium, alkanolammonium and glucammonium salts thereof;
  sulfonic acid derivatives of benzophenones, preferably 2-hydroxy-4-ethoxybenzophenone-5-sulfonic acid and salts thereof; and
  sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1,4'-tert.butylphenyl)-3-(4'-methoxyphenyl)-propane-1,3-dione, 4-tert.butyl-4'-methoxydibenzoyl methane (PARSOL® 1789) or 1-phenyl-3-(4'-isopropylphenyl)-propane-1,3-dione and the enamine compounds (BASF). The UV-A and UV-B filters may also be used in the form of mixtures. Particularly favorable combinations consist of the derivatives of benzoyl methane, for example 4-tert.butyl-4'-methoxydibenzoyl methane (PARSOL® 1789) and 2 cyano-3,3-phenylcinnamic acid-2-ethylhexyl ester (OCTOCRYLENE®), in combination with esters of cinnamic acid, preferably 4-methoxycinnamic acid-2-ethylhexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof Secondary Sun Protection Factors In addition to the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example, glycine, histidine, tyrosine, tryptophane) and derivatives thereof, imidazoles (for example, urocanic acid) and derivatives thereof, peptides, such as D,L-carnosine, D-carnosine, L-carnosine and derivatives thereof (for example, anserine), carotinoids, carotenes (for example, alpha-carotene, beta-carotene, lycopene) and derivatives thereof, chlorogenic acid and derivatives thereof, liponic acid and derivatives thereof (for example, dihydroliponic acid), aurothioglucose, propylthiouracil and other thiols (for example, thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts)

and sulfoximine compounds (for example, butionine sulfoximines, homocysteine sulfoximine, butionine sulfones, penta-, hexa- and hepta-thionine sulfoximine) in very small compatible dosages, also (metal) chelators (for example, alpha-hydroxyfatty acids, palmitic acid, phytic acid, lactoferrine), alpha-hydroxy acids (for example, citric acid, lactic acid, malic acid), humic acid, bile acid, bile extracts, bilirubin, biliverdin, EDTA, EGTA and derivatives thereof, unsaturated fatty acids and derivatives thereof (for example, linoleic acid, oleic acid), folic acid and derivatives thereof, ubiquinone and ubiquinol and derivatives thereof, vitamin C and derivatives thereof (for example, ascorbyl palmitate, Mg ascorbyl phosphate, ascorbyl acetate), tocopherols and derivatives (for example, vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid nordihydroguaiaretic acid, trihydroxybutyrophenone, uric acid and derivatives thereof, mannose and derivatives thereof, superoxide dismutase, titanium dioxide (for example, dispersions in ethanol, zinc and derivatives thereof (for example ZnO, $ZnSO_4$), selenium and derivatives thereof (for example, selenium methionine), stilbenes and derivatives thereof (for example, stilbene oxide, transstilbene oxide) and derivatives of these active substances like salts, esters, ethers, sugars, nucleotides, nucleosides, peptides and lipids.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Anti-microbial Agents

Suitable anti-microbial agents are, in principle, all substances effective against Gram-positive bacteria, such as, for example, 4 hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2--benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The sub-stances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic adds and esters thereof, such as, for example, citric acid, malic acid, tartaric acid or diethyl tartrate, and zinc glycinate.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), BAYPIVAL® (Climbazole), ketoconazole (4-acetyl-1-{4-[2-(2,4-dichlorophenyl)-r-2-(1H-imidazol-1-ylmethyl)-1,3-dioxolan-s-4-ylmethoxyphenyl}-piperazine, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, LAMEPON® UD (protein/undecylenic acid condensate), zinc pyrithione, aluminium pyrithione and magnesium pyrithione/dipyrithione magnesium sulfate.

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are:

glycerol;

alkylene glycols such as, for example, ethylene glycol, diethylene glycol, propylene glycol, butylene glycol, hexylene glycol and polyethylene glycols with an average molecular weight of 100 to 1000 Daltons;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol;

sugars containing 5 to 12 carbon atoms, for example glucose or sucrose;

amino sugars, for example glucamine; and dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Complexing Agents

The complexing agents used may be selected from EDTA, NTA, phosphonic acids, Triton B, turpinal and phenacetin. In addition, reducing agents such as, for example, ascorbic acid, sodium sulfate, sodium thiosulfate and the like may be present. Suitable alkalizing agents are ammonia, monoethanolamines, (L) arginine, AMP, etc.

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, dove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16256), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be pre-sent as a luminescent dye. These dyes are normally used in concentrations of 0.001 to 0.1% by weight, based on the mixture as a whole.

The total percentage content of auxiliaries and additives may be from 1 to 50% by weight, and is preferably from 5 to 40% by weight, based on the particular composition. The compositions may be produced by standard hot or cold processes.

EXAMPLES

Manufacturing Example M1

259 grams (1.8 moles) of caprylic acid, 511 grams (1.05 moles) of stearic acid and 0.3 grams of hypophosphoric acid were introduced into a stirred reactor and heated to 70° C. under a reduced pressure of 20 mbar. 447 grams (3 moles) of triethanolamine were then added dropwise in portions and, at the same time, the temperature was increased to 120° C. After the addition, the reaction mixture was heated to 160° C., the pressure was reduced to 3 mbar and the mixture was stirred under those conditions for 2.5 hours until the acid value had fallen to be low 5 mg KOH/g. The mixture was then cooled to 60° C., the vacuum was broken by introduction of nitrogen, and 0.6 grams of hydrogen peroxide was added in the form of a 30% by weight aqueous solution. For the quaternization step, the resulting ester was dissolved in 376 grams of isopropyl alcohol, and 357 grams (2.83 moles) of dimethyl sulfate were added to the resulting solution over a period of 1 hour at such a rate that the temperature did not rise above 65° C. After the addition, the mixture was stirred for another 2.5 hours, and the total nitrogen content was regularly checked by sampling. The reaction was terminated when constant total nitrogen content was reached. A product with a solids content of 80% b.w. was obtained.

Comparison Example C1

972 grams (3.6 moles) of partly hydrogenated palm oil fatty acid and 0.3 grams of hypophosphoric acid were introduced into a stirred reactor and heated to 70° C. under a reduced pressure of 20 mbar. 447 grams (3 moles) of triethanolamine were then added dropwise in portions and, at the same time, the temperature was increased to 120° C. After the addition, the reaction mixture was heated to 160° C., the pressure was reduced to 3 mbar and the mixture was stirred under those conditions for 2.5 hours until the acid value had fallen to below 5 mg KOH/g. The mixture was then cooled to 60° C., the vacuum was broken by introduction of nitrogen, and 0.6 grams of hydrogen peroxide was added in the form of a 30% by weight aqueous solution. For the quaternization step, the resulting ester was dissolved in 376 grams of isopropyl alcohol, and 357 grams (2.83 moles) of dimethyl sulfate were added to the resulting solution over a period of 1 hour at such a rate that the temperature did not rise above 65° C. After the addition, the mixture was stirred for another 2.5 hours, and the total nitrogen content was regularly checked by sampling. The reaction was terminated when constant total nitrogen content had been reached. A product with a solids content of 80% b.w. was obtained.

Determination of Viscosity

The asymmetric esterquats according to inventive example M1 and the comparison example C1 as an example for a symmetric esterquat were incorporated into an acidic hair care preparation consisting of 6% b.w. surfactant, 1% b.w. cetearyl alcohol and 1% b.w. non-ionic emulsifer (EUMULGIN® B2, Cognis Deutschland GmbH & Co. KG) (water added to 100% b.w.). The pH value of the formulations was adjusted to 3.5, while the formation of the emulsion was achieved by slightly stirring the mixtures at room temperature. In all cases homogenous emulsions were prepared. The viscosity of the products was determined according to the Brookfield method (RVT, 20° C., 10 rpm, Spindle 1). The results are compiled in Table 1. As one can see, the stability of the emulsions using the symmetric esterquat according to the present invention was lower, but more stable compared to the esterquat with symmetric side chains.

TABLE 1

Viscosities

| Example | Esterquat | Viscosities [mPas] | | |
|---|---|---|---|---|
| | | after 1 d | after 2 d | after 10 d |
| 1 | M1 | 5.000 | 4.900 | 4.900 |
| C1 | C1 | 6.200 | 5.900 | 4.300 |

Softening and Anti-static Properties

For testing the softening and anti-static properties the asymmetric esterquats according to the present the invention and the comparative symmetric esterquats were diluted with water to give 5% aqueous solutions. The tests were conducted using strands of brown hair (Alkinco #6634, length 12 cm, weight 1 gram). In order to determine the wet combablity the strands were tested before and after the treatment with 100 ml of the test solutions over a period of 5 minutes. Subsequently, the strands were washed over a period of 1 minute with 1 liter of water at an elevated temperature (about 38° C.). The results are compiled in Table 2; the test method is described in details in J. Soc. Cosm. Chem. 24, 782 (1973). The softening properties were determined by a panel of 6 trained people. The results also compiled in Table 2 represent the average values from three test cycles. The lower the numbers the better the softness of the strands. As one can see, the new esterquats with asymmetric side chains exhibit an improved softening behavior and reduce the force for wet combing more than the comparable esterquat with symmetric side chains.

TABLE 2

Softening and wet combability

| Example | Esterquat | Softening | Wet combability [mJ] | | |
|---|---|---|---|---|---|
| | | | prior to treatment | after treatment | Difference |
| 2 | M1 | 1.8 | 69.6 | 20.4 | 49.2 |
| C2 | C1 | 2.0 | 61.0 | 16.2 | 44.8 |

In the following Table 3 some formulation examples are given.

TABLE 3

Cosmetic compositions (Water and preservatives adding to 100% b.w.)

| Composition (INCI) | 1 | 2 | 3 | 4 | 5 | 6 | 7 | 8 | 9 | 10 |
|---|---|---|---|---|---|---|---|---|---|---|
| Texapon ® NSO<br>Sodium Laureth Sulfate | — | — | — | — | — | — | 38.0 | 38.0 | 25.0 | — |
| Texapon ® SB 3<br>Disodium Laureth Sulfosuccinate | — | — | — | — | — | — | — | — | 10.0 | — |
| Plantacare ® 818<br>Coco Glucosides | — | — | — | — | — | — | 7.0 | 7.0 | 6.0 | — |
| Plantacare ® PS 10<br>Sodium Laureth Sulfate (and) Coco Glucosides | — | — | — | — | — | — | — | — | — | 16.0 |
| Dehyton ® PK 45<br>Cocamidopropyl Betaine | — | — | — | — | — | — | — | — | 10.0 | — |
| Asymmetric Esterquat according to Example M1 | 2.0 | 2.0 | 2.0 | 2.0 | 4.0 | 4.0 | 2.0 | 2.0 | 2.0 | 2.0 |
| Dehyquart L ® 80<br>Dicocoylmethylethoxymonium Methosulfate (and) Propylenglycol | 1.2 | 1.2 | 1.2 | 1.2 | 0.6 | 0.6 | — | — | — | — |
| Eumulgin ® B2<br>Ceteareth-20 | 0.8 | 0.8 | — | 0.8 | — | 1.0 | — | — | — | — |
| Eumulgin ® VL 75<br>Lauryl Glucoside (and) Polyglyceryl-2 Polyhydroxystearate (and) Glycerin | — | — | 0.8 | — | 0.8 | — | — | — | — | — |
| Lanette ® O<br>Cetearyl Alcohol | 2.5 | 2.5 | 2.5 | 2.5 | 3.0 | 2.5 | — | — | — | — |
| Cutina ® GMS<br>Glyceryl Stearate | 0.5 | 0.5 | 0.5 | 0.5 | 0.5 | 1.0 | — | — | — | — |
| Cetiol ® HE<br>PEG-7 Glyceryl Cocoate | 1.0 | — | — | — | — | — | — | — | 1.0 | — |
| Cetiol ® PGL<br>Hexyldecanol (and) Hexyldecyl Laurate | — | 1.0 | — | — | 1.0 | — | — | — | — | — |
| Cetiol ® V<br>Decyl Oleate | — | — | — | 1.0 | — | — | — | — | — | — |
| Eutanol ® G<br>Octyldodecanol | — | — | 1.0 | — | — | 1.0 | — | — | — | — |
| Nutrilan ® Keratin W<br>Hydrolyzed Keratin | — | — | — | 2.0 | — | — | — | — | — | — |
| Lamesoft ® LMG<br>Glyceryl Laurate (and) Potassium Cocoyl Hydrolyzed Collagen | — | — | — | — | — | — | 3.0 | 2.0 | 4.0 | — |
| Euperlan ® PK 3000 AM<br>Glycol Distearate (and) Laureth-4 (and) Cocamidopropyl Betaine | — | — | — | — | — | — | — | 3.0 | 5.0 | 5.0 |
| Generol ® 122 N<br>Soja Sterol | — | — | — | — | 1.0 | 1.0 | — | — | — | — |

TABLE 3-continued

Cosmetic compositions (Water and preservatives adding to 100% b.w.)

| | | | | | | | | | | |
|---|---|---|---|---|---|---|---|---|---|---|
| Hydagen ® CMF Chitosan | 1.0 | 1.0 | 1.0 | 1.0 | 1.0 | 1.0 | 1.0 | 1.0 | 1.0 | 1.0 |
| Copherol ® 1250 Tocopherol Acetate | — | — | 0.1 | 0.1 | — | — | — | — | — | — |
| Arlypon ® F Laureth-2 | — | — | — | — | — | — | 3.0 | 3.0 | 1.0 | — |
| Sodium Chloride | — | — | — | — | — | — | — | 1.5 | — | 1.5 |

| Composition (INCI) | 11 | 12 | 13 | 14 | 15 | 16 | 17 | 18 | 19 | 20 |
|---|---|---|---|---|---|---|---|---|---|---|
| Texapon ® NSO Sodium Laureth Sulfate | 20.0 | 20.0 | 12.4 | — | 25.0 | 11.0 | — | — | — | — |
| Texapon ® K 14 S Sodium Myreth Sulfate | — | — | — | — | — | — | — | — | 11.0 | 23.0 |
| Texapon ® SB 3 Disodium Laureth Sulfosuccinate | — | — | — | — | — | 7.0 | — | — | — | — |
| Plantacare ® 818 Coco Glucosides | 5.0 | 5.0 | 4.0 | — | — | — | — | — | 6.0 | 4.0 |
| Plantacare ® 2000 Decyl Glucoside | — | — | — | — | 5.0 | 4.0 | — | — | — | — |
| Plantacare ® PS 10 Sodium Laureth Sulfate (and) Coco Glucosides | — | — | — | 40.0 | — | — | 16.0 | 17.0 | — | — |
| Dehyton ® PK 45 Cocamidopropyl Betaine | 20.0 | 20.0 | — | — | 8.0 | — | — | — | — | 7.0 |
| Eumulgin ® B1 Ceteareth-12 | — | — | — | — | 1.0 | — | — | — | — | — |
| Eumulgin ® B2 Ceteareth-20 | — | — | — | 1.0 | — | — | — | — | — | — |
| Lameform ® TGI Polyglyceryl-3 Isostearate | — | — | — | 4.0 | — | — | — | — | — | — |
| Dehymuls ® PGPH Polyglyceryl-2 Dipolyhydroxystearate | — | — | 1.0 | — | — | — | — | — | — | — |
| Monomuls ® 90-L 12 Glyceryl Laurate | — | — | — | — | — | — | — | — | 1.0 | 1.0 |
| Cetiol ® HE PEG-7 Glyceryl Cocoate | — | 0.2 | — | — | — | — | — | — | — | — |
| Eutanol ® G Octyldodecanol | — | — | — | 3.0 | — | — | — | — | — | — |
| Nutrilan ® Keratin W Hydrolyzed Keratin | — | — | — | — | — | — | — | — | 2.0 | 2.0 |
| Nutrilan ® I Hydrolyzed Collagen | 1.0 | — | — | — | — | 2.0 | — | 2.0 | — | — |
| Lamesoft ® LMG Glyceryl Laurate (and) Potassium Cocoyl Hydrolyzed Collagen | — | — | — | — | — | — | — | — | 1.0 | — |
| Lamesoft ® 156 Hydrogenated Tallow Gyceride (and) Potassium Cocoyl Hydrolyzed Collagen | — | — | — | — | — | — | — | — | — | 5.0 |
| Gluadin ® WK Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM Glycol Distearate (and) Laureth-4 (and) Cocamidopropyl Betaine | 5.0 | 3.0 | 4.0 | — | — | — | — | 3.0 | 3.0 | — |
| Arlypon ® F Laureth-2 | 2.6 | 1.6 | — | 1.0 | 1.5 | — | — | — | — | — |
| Asymmetric Esterquat according to Example M1 | 2.0 | 2.0 | 2.0 | 2.0 | 4.0 | 4.0 | 2.0 | 2.0 | 2.0 | 2.0 |
| Hydagen ® CMF Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerin (86 Gew.-% ig) | — | 5.0 | — | — | — | — | — | 1.0 | 3.0 | — |

(1-4) Hair cure, (5-6) Conditioner, (7-8) Shower bath, (9) Shower gel, (10) Washing lotion (11-14) Shower bath Two-in-One), (15-20) Shampoo

What is claimed is:

1. A process for preparing esterquats comprising the steps of:
   (a) reacting one or more alkanolamines with a mixture consisting of:
      (i) 30-70% by weight of one or more $C_6$-$C_{10}$ monocarboxylic acids, selected from the group consisting of caproic acid, caprylic acid, caprinic acid, and mixtures thereof, and
      (ii) 70-30% by weight of one or more $C_{12}$-$C_{22}$ monocarboxylic acids, selected from the group consisting of lauric acid, myristic acid, palmitic acid, stearic acid, oleic acid, behenic acid, erucic acid, and mixtures thereof, and
   (b) quaternizing the resulting esters with one or more alkylation agents.

2. The process according to claim 1, further comprising the step of alkoxylating the esters prior to the step of quaternizing.

3. A process for preparing esterquats comprising the steps of:
(a) esterifying a mixture of carboxylic acids with one or more alkanolamines to form a mixture of alkanolamine mono-, di- and tri-esters, wherein the mixture of carboxylic acids consists of:
   (i) 30-70% by weight of one or more $C_6$-$C_{10}$ monocarboxylic acids, selected from the group consisting of caproic acid, caprylic acid, caprinic acid, and mixtures thereof, and
   (ii) 70-30% by weight of one or more $C_{12}$-$C_{22}$ monocarboxylic acids, selected from the group consisting of lauric acid, myristic acid, palmitic acid, stearic acid, oleic acid, behenic acid, erucic acid, and mixtures thereof; and
(b) quaternizing the esters with one or more alkylation agents.

4. The process according to claim 3, further comprising the step of alkoxylating the esters prior to the step of quaternizing.

5. The process according to claim 3, wherein the one or more alkanolamines correspond to general formula (I):

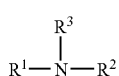
(I)

wherein $R^1$ represents a hydroxyethyl group, and $R^2$ and $R^3$ independently represent hydrogen, methyl or hydroxyethyl.

6. The process according to claim 3, wherein said one or more alkanolamines comprises triethanolamine.

7. The process according to claim 3, wherein the mixture of carboxylic acids consists of caprylic acid and stearic acid.

8. The process according to claim 3, wherein in the mixture of monocarboxylic acids, the one or more $C_6$-$C_{10}$ monocarboxylic acids and the one or more $C_{12}$-$C_{22}$ monocarboxylic acids are present in molar ratios of 30:70 to 70:30.

9. The process according to claim 3, wherein the mixture of carboxylic acids consists of caprylic acid and stearic acid in molar ratios of 30:70 to 70:30.

10. The process according to claim 3, wherein the one or more alkylation agents are selected from the group consisting of alkyl halides, benzyl halides, and dialkyl sulfates.

11. The process according to claim 10, wherein the alkylation agents are selected from methyl chloride, benzyl chloride, and dimethyl sulfate.

12. The process according to claim 3, wherein 95 to 105 mol % of the alkylation agent, based on the molar amount of nitrogen in the ester mixture, is used.

13. The esterquats obtained according to the process of claim 1.

14. A cosmetic composition comprising at least one esterquat obtained according to the process of claim 1.

15. A skin care composition comprising at least one esterquat obtained according to the process of claim 1.

16. A hair care composition comprising at least one esterquat obtained according to the process of claim 1.

17. A shampoo or a conditioner comprising at least one esterquat obtained according to the process of claim 1.

* * * * *